United States Patent [19]

Wang et al.

[11] Patent Number: 5,693,813

[45] Date of Patent: Dec. 2, 1997

[54] PROCESS FOR PREPARATION OF 4H-4-OXO-QUINOLIZINE-3-CARBOXYLIC ACID

[75] Inventors: Wei-Bo Wang; Francis A. J. Kerdesky, both of Grayslake; Chi-Nung W. Hsiao; Qun Li, both of Libertyville, all of Ill.; Daniel T. Chu, Santa Clara, Calif.

[73] Assignee: Abbott Laboratories, Abbott Park, Ill.

[21] Appl. No.: 806,806

[22] Filed: Feb. 26, 1997

[51] Int. Cl.$^6$ ................................................ C07D 455/02
[52] U.S. Cl. ............................................. 546/138; 546/112
[58] Field of Search ................................................ 546/138

[56] References Cited

U.S. PATENT DOCUMENTS 5,599,816  2/1997  Chu et al. .................................. 514/254

FOREIGN PATENT DOCUMENTS 9116894  11/1991  WIPO .
9510519  4/1995  WIPO .

*Primary Examiner*—Alan L. Rotman
*Assistant Examiner*—Charanjit S. Aulakh
*Attorney, Agent, or Firm*—Mona Anand

[57] ABSTRACT

A process for the preparation of a compound having the formula:

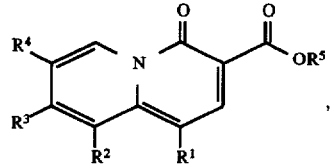

wherein $R^1$, $R^2$, $R^3$, $R^4$, and $R^5$ are defined, from an enamine by chain expansion and ring closure followed by additional derivatization, treatment with a 3-alkoxyl-acryloyl compound, another ring closure, and converting a hydroxyl group to a leaving group.

10 Claims, No Drawings

PROCESS FOR PREPARATION OF 4H-4-OXO-QUINOLIZINE-3-CARBOXYLIC ACID

TECHNICAL FIELD

The present invention relates to a process for the preparation of 4H-4-oxo-quinolizine-3-carboxylic acid derivatives, which have use as intermediates in the preparation of 4H-4-oxo-quinolizine-3-carboxylic acid antibacterial agents (also known as pyridone antibiotics).

BACKGROUND OF THE INVENTION

The therapeutic use of certain 4H-4-oxo-quinolizine-3-carboxylic acid derivatives as antibacterial agents has been described by Chu et al. (PCT patent applications WO 9116894, published Nov. 14, 1991, and WO 9510519, published Apr. 20, 1995). One key intermediate for the preparation of these compounds is the ethyl ester of 8-chloro-1-cyclopropyl-7-fluoro-9-methyl-4H-4-oxo-quinolizine-3-carboxylic acid, having the formula:

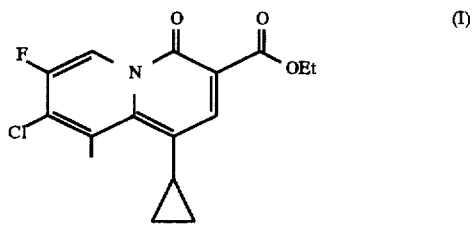

(I)

The process for the preparation of compound (I), as described in Scheme 12 of PCT patent application WO 9510519, involves a ten-step synthesis which requires the expensive starting material, 3-chloro-2,4,5,6-tetrafluoropyridine.

More efficient processes are needed for the preparation of this key intermediate and related compounds useful in the synthesis of pyridone antibiotics to ensure that the products are readily available to the public.

SUMMARY OF THE INVENTION

The present invention describes an efficient seven-step process for the preparation of compounds having the formula (II),

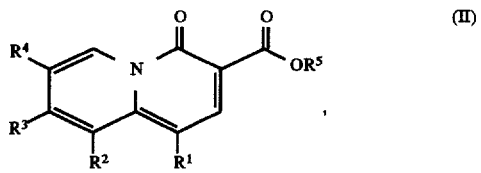

(II)

wherein $R^1$ is selected from the group consisting of $C_1$–$C_6$-alkyl, $C_2$–$C_6$-alkenyl, $C_2$–$C_6$-alkynyl, $C_3$–$C_6$-cycloalkyl, phenyl, fluorophenyl, difluorophenyl, nitrophenyl, dinitrophenyl, and fluoropyridyl, $R^2$ is $C_1$–$C_3$-alkyl or cyclopropyl, $R^3$ is chlorine, bromine, iodine, methylsulfonate, trifluoromethylsulfonate or toluenesulfonate, $R^4$ is fluorine, chlorine, bromine, or iodine, and $R^5$ is $C_1$–$C_6$-alkyl. Compounds of formula (II) are useful as intermediates in the preparation of 4H-4-oxo-quinolizine-3-carboxylic acid antibiotic agents.

In one aspect of the present invention is a process for the preparation of 4H-4-oxo-quinolizine-3-carboxylic acid derivatives having the formula:

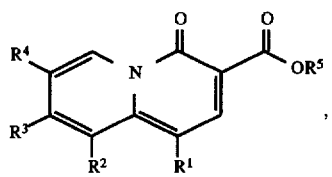

wherein $R^1$, $R^2$, $R^3$, $R^4$ and $R^5$ are as defined above; the method comprising:

(a) treating a compound having the formula:

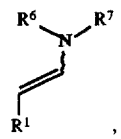

wherein $R^1$ is as defined above, $R^6$ and $R^7$ are $C_1$–$C_6$-alkyl, or $R^6$ and $R^7$ are taken together with the nitrogen atom to which they are connected to form a morpholinyl, pyrrolidinyl or piperidinyl ring, with an acid chloride $R^2$—$CH_2$—CO—Cl, wherein $R^2$ is as described above, and isolating a first intermediate compound having the structure:

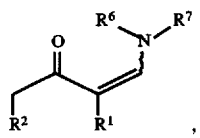

wherein $R^1$, $R^2$, $R^6$ and $R^7$ are as described above;

(b) treating the first intermediate compound sequentially with a base, then with 2-cyanoacetamide, and isolating a second intermediate compound having the structure:

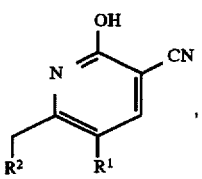

wherein $R^1$ and $R^2$ are as described above;

(c) hydrolyzing the cyano group of the second intermediate compound with an acid in an alcohol solvent $R^5$—OH, wherein $R^5$ is as described above, and isolating a third intermediate compound having the structure:

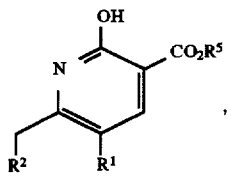

wherein $R^1$ and $R^2$ are as described above and $R^5$ is $C_1$–$C_6$-alkyl;

(d) treating the third intermediate compound with $R^8X$, wherein $R^8$ is $C_1$–$C_6$-alkyl, benzyl, substituted benzyl, or trialkylsilyl, and X is chlorine, bromine, iodine, methylsulfonate, trifluoromethylsulfonate or toluenesulfonate, and isolating a fourth intermediate compound having the structure:

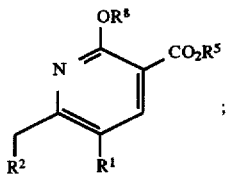

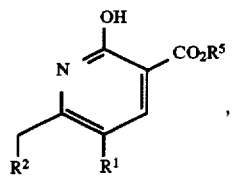

(e) treating the fourth intermediate compound sequentially with an alkali metal base, then with a 3-alkoxyacryloyl compound having the formula:

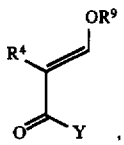

wherein $R^4$ is as described above, $R^9$ is $C_1$–$C_6$-alkyl and Y is chloride, bromide, cyano, alkoxy or imidazolyl and isolating a fifth intermediate compound having the structure:

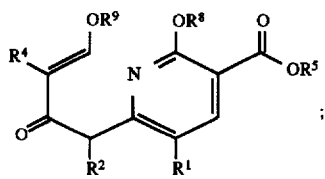

(f) cyclizing the fifth intermediate compound with a catalytic amount of acid, and isolating the sixth intermediate compound having the structure:

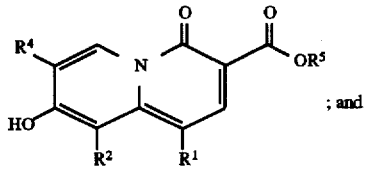

(g) treating the sixth intermediate compound with a halogenating or sulfonating agents, and isolating the desired compound.

In an alternate aspect of the invention is a process similar to that described above, wherein steps (b) and (c) are replaced by a single step which consists of reacting the first intermediate compound having the structure:

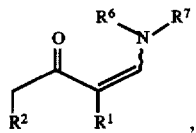

wherein $R^1$, $R^2$, $R^6$ and $R^7$ are as described above, with an ester of malonamic acid ($R^5O_2C$—$CH_2$—$CO$—$NH_2$, wherein $R^5$ is as described above) in the presence of a base, to prepare the intermediate compound having the formula:

then carrying the intermediate forward as described in steps (d) through (g) above, and isolating the desired product.

DETAILED DESCRIPTION OF THE INVENTION

The term "$C_1$–$C_6$-alkyl" refers to saturated, straight- or branched-chain hydrocarbon radicals containing from one to six carbon atoms including, but not limited to, methyl, ethyl, propyl, i-propyl, n-butyl, tert-butyl, pentyl, neopentyl and hexyl. The term "$C_1$–$C_3$-alkyl" refers to alkyl radicals containing from one to three carbon atoms including methyl, ethyl, propyl, and i-propyl.

The term "$C_2$–$C_6$-alkenyl", as used herein, refers to mono-unsaturated straight- or branched-chain hydrocarbon radicals containing from two to six carbon atoms including, but not limited to, vinyl, propenyl, n-butenyl, i-butenyl, n-pentenyl, and n-hexenyl.

The term "$C_2$–$C_6$-alkynyl", as used herein, refers to straight- or branched-chain hydrocarbon radicals possessing a single triple bond and containing from two to six carbon atoms including, but not limited to, ethynyl, propynyl, n-butynyl, n-pentynyl, and n-hexynyl.

The term "$C_3$–$C_6$-cycloalkyl" refers to a saturated monocyclic hydrocarbon radical having from three to six carbon atoms in the ring. Examples of cycloalkyl radicals include cyclopropyl, cyclobutyl, cyclopentyl and cyclohexyl.

The term "substituted benzyl", as used herein, refers to a benzyl group substituted with a chloro, bromo, methoxy, or methyl. Examples of substituted benzyl include, but are not limited to, 4-chlorobenzyl, 4-bromobenzyl, 4-methoxybenzyl, 4-methylbenzyl, and the like.

The term "trialkylsilyl", as used herein, refers to a silicon atom independently substituted with three $C_1$–$C_6$-alkyl radicals. Examples of trialkylsilyl moieties include, but are not limited to, trimethylsilyl, dimethyl-t-butylsilyl, and the like.

The term "aprotic solvent" or "aprotic organic solvent", as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Solvents suitable for the preparation of the compounds described herein are well known to those skilled in the art, and it will be obvious to such persons that individual solvents or mixtures thereof may be preferred for specific compounds and reaction conditions, depending upon such factors as the solubility of reagents, reactivity of reagents and preferred temperature ranges, for example. Further discussions of solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, N.Y., 1986.

Abbreviations which have been used in the descriptions of the schemes and the examples that follow are: n-BuLi for n-butyllithium; LDA for lithium diisopropylamide; TBSCl for t-butyldimethylsilyl chloride; THF for tetrahydrofuran.

Synthetic Methods

The processes of the present invention for preparing compounds (II) will be better understood in connection with the following synthetic Schemes 1–5 below which illustrate in more detail the specific reactions of the processes.

It will be understood by those skilled in the art that tautomeric forms of certain of the illustrated compounds may exist under the conditions of the invention, and that the invention is not be limited in any way by the choice of the tautomers shown in the Schemes for purposes of illustration. In the Schemes below and in the processes illustrated elsewhere herein the use of a wavy line ⸾ indicates that the substituent group attached to the double bond by the wavy line may be in either the cis- or trans- position with respect to the substituent group at the opposite end of the double bond.

attached to form a morpholinyl, pyrrolidinyl and piperidinyl ring. Illustrative of $R^1$ groups, but not limited thereto, are methyl, ethyl, propyl, butyl, iso-butyl, t-butyl, pentyl, hexyl, vinyl, allyl, 2-butenyl, 4-pentenyl, 3-hexenyl, ethynyl, 2-propynyl, butynyl, pentynyl, hexynyl, and the like. Illustrative of $R^6$ and $R^7$ groups when taken separately, but not limited thereto, are methyl, ethyl, propyl, butyl, iso-butyl, t-butyl, pentyl, hexyl, and the like. The reaction is preferably carded out in the presence of a base, such as for example, triethylamine, trimethylamine, diisopropylethylamine, N-methylpiperidine, N-methylpyrrolidine, N-methylmorpholine, pyridine and the like, or another equivalent of the enamine, or in the presence of a Lewis acid catalyst, such as stannic chloride, for example. The reaction may be carried out at a temperature of from about $-20°$ C. to about $80°$ C. for from about 4 to about 48 hours in an aprotic solvent such as chloroform, methylene chloride, acetonitrile, benzene, toluene, ether, dioxane, pyridine, hexane or the like.

Compound 2 is sequentially treated with a base, then with 2-cyanoacetamide to prepare compound 3. Illustrative of a suitable base, but not limited thereto, are piperidine acetate,

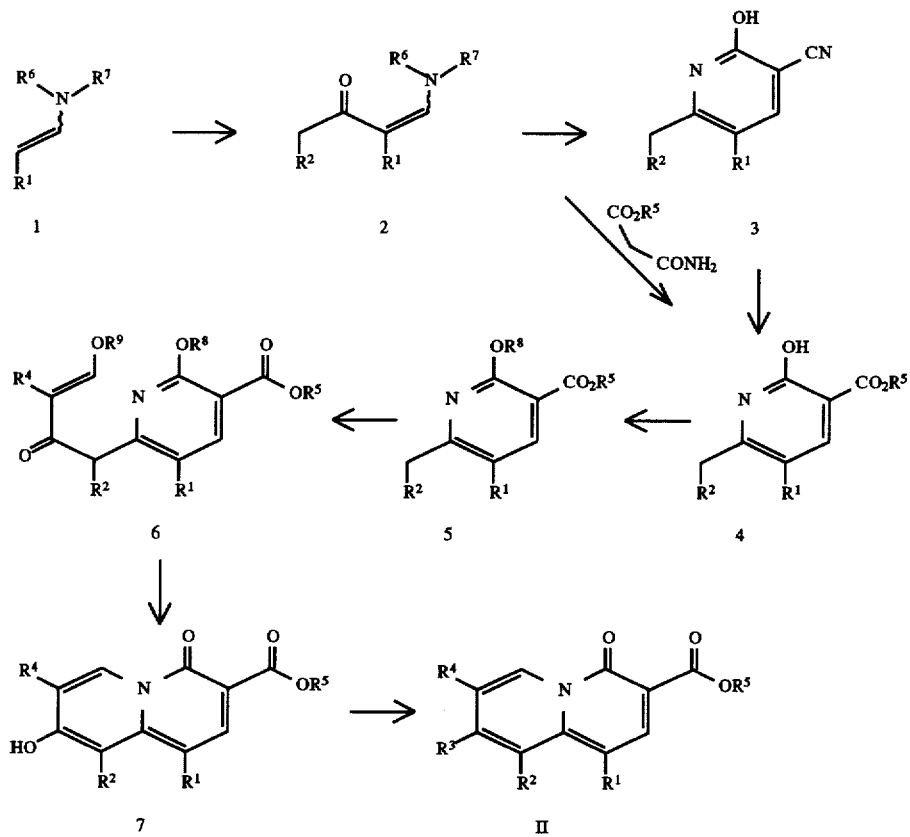

Scheme 1

In accordance with Scheme 1, an enamine compound 1 is treated with an acid chloride $R^2$—$CH_2$—CO—Cl to form the compound 2. In compounds 1 and 2, $R^1$ may be selected from the group consisting of $C_1$–$C_6$-alkyl, $C_2$–$C_6$-alkenyl, $C_2$–$C_6$-alkynyl, $C_3$–$C_6$-cycloalkyl, phenyl, fluorophenyl, difluorophenyl, nitrophenyl, dinitrophenyl and fluoropyridyl, and $R^2$ may be $C_1$–$C_3$-alkyl or cyclopropyl, and $R^6$ and $R^7$ may independently be $C_1$–$C_6$-alkyl, or $R^6$ and $R^7$ taken together with the nitrogen atom to which they are potassium or sodium carbonate, sodium methoxide, sodium ethoxide, sodium hydride, potassium tert-butoxide, triethylamine, diisopropylethylamine, and the like. The reaction may be carded out at a temperature of about $23°$ C. to reflux for from about 4 to about 24 hours in a polar solvent, such as ethanol, methanol, water, acetonitrile, tetrahydrofuran, dimethylformamide, dimethyl sulfoxide, 1,1,3,3-tetramethoxypropane, 2-propanol, pyridine and the like. Alternately, the reaction may be performed with the use a catalyst such as tetrabutylammonium hydrogen sulfate in place of the base.

The cyano group of compound 3 is then hydrolyzed with an acid in a suitable alcohol to prepare compound 4, wherein $R^5$ is $C_1-C_6$-alkyl. Illustrative of suitable alcohol solvents, but not limited thereto, are methanol, ethanol, propanol, iso-propanol, butanol, t-butanol, pentanol, hexanol, and the like. Most commonly the acid may be HCl, $H_2SO_4$, p-toluenesulfonic acid, trifluoroacetic acid, or the like, but other suitable acids such as are known to the art may be substituted. The reaction is routinely carried out at the reflux temperature of the alcohol for about 4 to about 24 hours.

Alternately, compound 2 may be treated with an ester of malonamic acid, $R^5-O-CO-CH_2-CO-NH_2$, in the presence of a base, such as is used in the cyanoacetamide reaction described above, to form compound 4 directly.

Compound 4 is then protected at the hydroxy position to give compound 5 by treatment with $R^8X$, wherein $R^8$ is methyl, ethyl, benzyl, substituted benzyl, trialkylsilyl, or the like, and X is chlorine, bromine, iodine, methylsulfonate, trifluoromethylsulfonate or toluenesulfonate. Illustrative of trialkylsilyl, but not limited thereto, are trimethylsilyl, dimethyl-t-butylsilyl, and the like. This reaction may be performed in an aprotic solvent at from 0° C. to reflux temperature for from about 4 to about 48 hours.

Compound 5 is then treated sequentially with an alkali metal base then with a 3-alkoxy-acryloyl compound having the formula:

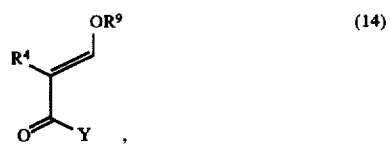

(14)

wherein $R^4$ is F, Cl, Br or I, and is preferably F, $R^9$ is $C_1-C_6$-alkyl and Y is chloride, bromide, cyano, alkoxy or imidazolyl, to give compound 6. Illustrative of an alkali metal base, but not limited thereto, are sodium, potassium, lithium hexamethylsilizane, n-butyllithium, LDA, and the like. The reaction may be performed in an aprotic solvent at about −78° C. to about 0° C. for about 2 to about 6 hours. The preparation of reagent 14 is described in Scheme 5 below.

Compound 6 is then treated with a catalytic amount of acid to close the ring and give compound 7. An acid such as HCl, $H_2SO_4$, p-toluenesulfonic acid, trifluoroacetic acid, acetic acid, or the like, may be employed, and the reaction is normally accomplished at from room temperature to reflux temperature in a suitable organic solvent over approximately a 4 to 24 hour period.

Compound 7 is then treated with halogenating agents to replace the 2-hydroxyl group with a halogen atom and give compound II ($R^3$=Cl, Br). Illustrative of a halogenating agents, but not limited thereto, are $PCl_5$, $POCl_3$, $PBr_3$, $SOBr_2$ or the like; or the 2-hydroxy group can be converted to methylsulfonate, trifluoromethylsulfonate or toluenesulfonate to give compound II ($R^3$=OMs, OTs, or OTf) under appropriate conditions. Illustrative of an appropriate condition, but not limited thereto, are methanesulfonyl chloride, toluenesulfonyl chloride, or trifluoroacetic anhydride in the presence of a suitable base such as pyridine, triethyl amine and the like. The reactions may be performed in an aprotic solvent at a temperature from about 0° C. to reflux for about 4–24 hours.

In a preferred embodiment of the process according to Scheme 1, $R^1$ is cyclopropyl, $R^2$ is methyl, $R^3$ is chloro, $R^4$ is fluoro, and $R^5$ is ethyl.

In another preferred embodiment of the process according to Scheme 1, $R^6$ and $R^7$ are taken together with the atom to which they are connected to form a morpholinyl ring.

In a more preferred embodiment of the process according to Scheme 1, in step (a) the reaction is performed in the presence of a base at a temperature of from about −20° C. to about 80° C. for from about 4 to about 48 hours; in step (b), the reaction is performed at a temperature of about 23° C. to reflux for from about 4 to about 24 hours; in step (c) the reaction is performed at the reflux temperature of the solvent for about 4 to about 24 hours; in step (d) the reaction is performed at from about 0° C. to reflux temperature for from about 4 to about 48 hours; in step (e) the reaction is performed at about −78° C. to about 0° C. for about 2 to 6 hours; in step (f) the reaction is performed at reflux temperature for from about 4 to about 24 hours; and in step (g) the reaction is performed at room temperature for about 4 hours to about 24 hours.

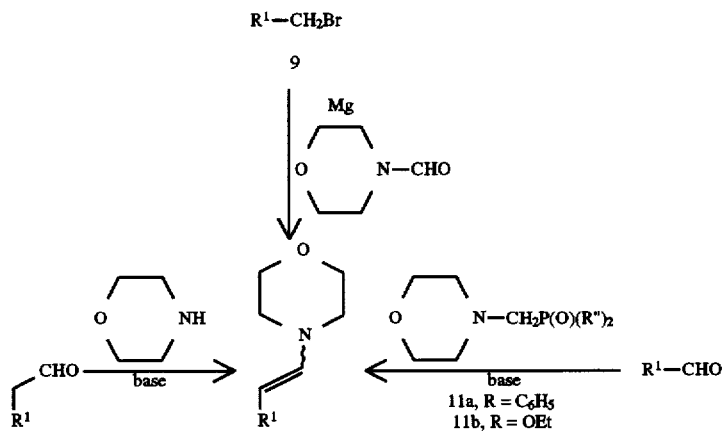

Scheme 2

The starting material 1 for the process of the invention may be prepared according to Scheme 2. The appropriate aldehyde 8 may be reacted with morpholine in the presence of a base, such as K₂CO₃, for example, at ambient or elevated temperature. Alternately, alkyl bromide 9 may be reacted with magnesium under Grignard reaction conditions and coupled with N-formylmorpholine to prepare compound 1. In a further alternate method, an aldehyde 10 may be treated with diphenylphosphine oxide 11a or diethyl phosphonate 11b in the presence of an alkyllithium base, such as for example, n-butyllithium, at a temperature of from about −70° C. to about 0° C. to prepare the enamine 1.

fluoro, R⁶ and R⁷ are taken together with the nitrogen atom to which they are connected to form a morpholinyl ring, R⁵ is ethyl, R⁸ is t-butyldimethylsilyl, and R⁹ is ethyl as described in Scheme 1 above. The reaction conditions are as described in Scheme 1.

Alternately, compound 2A may be treated with the ethyl ester of malonamic acid, ethyl-O—CO—CH₂—CO—NH₂, in the presence of a base, such as is used in the cyanoacetamide reaction described above, to form compound 4A directly.

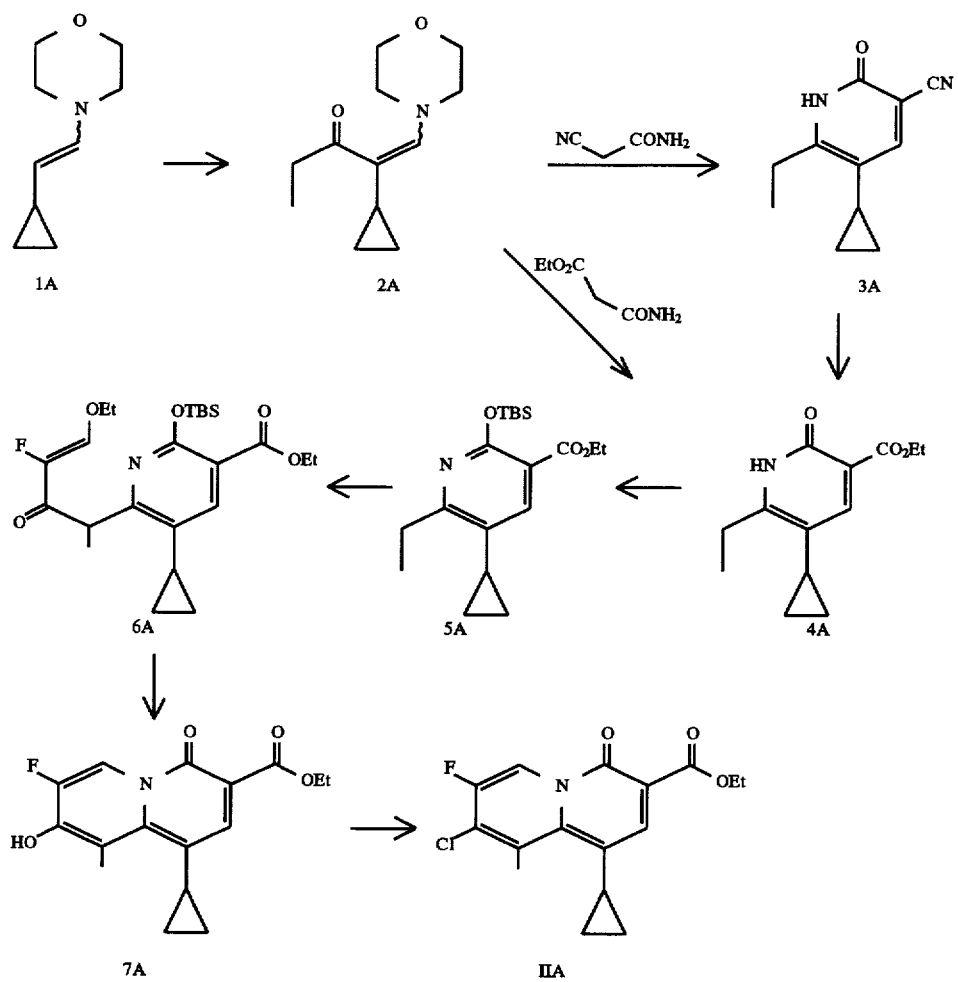

In accordance with Scheme 3, the preparation of a preferred embodiment of the process of Scheme 1 is illustrated, wherein R¹ is cyclopropyl, R² is methyl, R³ is chloro, R⁴ is

Scheme 4

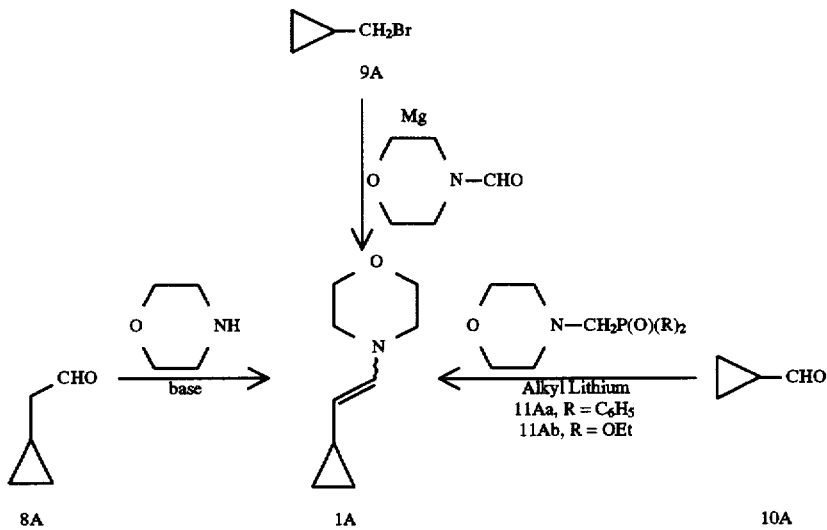

In Scheme 4 are shown several methods by which the preferred starting material 1A (compound 1 of Scheme 1 wherein $R^1$ is cyclopropyl, and $R^6$ and $R^7$ are taken together with the nitrogen atom to which they are connected to form a morpholinyl ring) may be prepared. By one reaction, 2-cyclopropylacetaldhyde (8A) is reacted with morpholine at ambient or elevated temperature in the presence of a base such as potassium carbonate. In another instance cyclopropylmethyl bromide (9A) is treated with Mg and N-formylmorpholine under the Grignard reaction conditions. Alternately still, cyclopropylcarboxaldehyde (10A) may be reacted with a morpholine N-methylphosponate reagent under the Wittig-type conditions.

Scheme 5

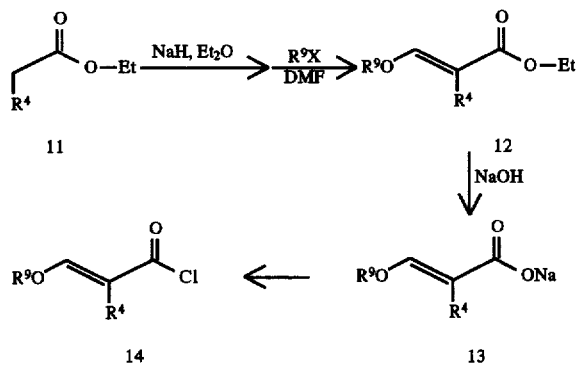

In accordance with Scheme 5, the starting material (11), including the preferred compound wherein $R^4$ is F, i.e., ethyl fluoroacetate, is treated sequentially under anhydrous conditions with first an alkali metal base, such as, for example, NaH in ether, then after removal of the solvent reaction of the residue is redissolved in DMF and reacted with an $R^9X$ compound wherein $R^9$ is $C_1$–$C_6$-alkyl, preferably ethyl, and X is chlorine, bromine, iodine, methylsulfonyl, trifluoromethylsulfonyl or toluenesulfonyl, to prepare compound 12. The reactions are preferably run at about 0° C. for from about 1 to about 16 hours. Compound 12 is converted to the sodium salt 13 by treatment with 2N NaOH at reflux for from 1 to 4 hours, and compound 13 is dried and converted to the acyl chloride 14 by treatment with thionyl chloride in ether or a similar suitable solvent at reflux for from about 2 to about 8 hours.

In a preferred aspect of the invention is an alternate process similar to that described in Scheme 3 above, wherein steps (b) and (c) are replaced by a single step which consists of reacting the first intermediate compound having the structure:

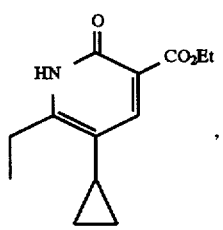

with the ethyl ester of malonamic acid (ethyl-O—CO—$CH_2$—CO—$NH_2$) in the presence of a base such as potassium carbonate, piperidine acetate, piperidine, triethylamine, or sodium ethoxide and at a temperature of about 23° C. to reflux in a solvent such as ethanol, tetrahydrofuran, acetonitrile and the like, for about 4 to about 24 hours to prepare the intermediate compound having the formula:

then carrying the intermediate forward as described in steps (d) through (g) and isolating the desired product.

Experimental

The processes of the present invention will be better understood in connection with the following examples, which are intended as an illustration of and not a limitation upon the scope of the invention.

EXAMPLE 1

(Compound 1A, Scheme 3)

Preparation of Starting Material 1-(2-cyclopropylethenyl)morpholine

Method 1A

Cyclopropaneacetaldehyde (8A, 168 mg, 2 mmol, prepared according to C. A. Hendrick, U.S. Pat. No. 3,876,682) was added dropwise to a cooled mixture of morpholine (435 mg, 5 mmol) and potassium carbonate (276 mg, 2 mmol). After stirring for 12 hours at 23° C. the reaction mixture was filtered, and the flask and solid were washed with ether. The ether extracts were combined, concentrated and distilled to afford the title compound as a colorless oil (1A, 189 mg, 62%). $^1$H NMR (300 MHz, CDCl$_3$): δ0.26 (m, 2H), 0.63 (m, 2H), 1.30 (m, 1H), 2.78 (t, 4H), 3.71 (t, 4H), 4.18 (dd, 1H), 5.92 (d, 1H); MS (DCI/NH$_3$) m/e 154 (M+H)$^+$, 168 (M+NH$_4$)$^+$. Anal. Calcd for C$_9$H$_{15}$NO: C, 70.54; H, 9.86; N, 9.14. Found C, 70.84; H, 9.90; N, 8.92.

Method 1B

To a solution of (bromomethyl)cyclopropane (9A, 1.35 g, 10 mmol) in ether (5 mL) was added magnesium timings (240 mg, 10 mmol) at 23° C. under nitrogen. The reaction mixture was refluxed for 6 hours. The resulted Grignard reagent was added to N-formylmorpholine (1.5 g, 13 mmol) in tetrahydrofuran (5 mL) at −15° C., and after 30 min the mixture was allowed to warm to room temperature. The title compound was isolated as a colorless oil by precipitating inorganic material with hexane and distilling the supernatant (1A, 0.98 g, 64%).

Method 1C n-BuLi (40 mL of 2.5M hexane solution, 0.1 mol) was added dropwise to a suspension of N-morpholinylmethyl diphenylphosphine oxide (11Aa, 30 g, 0.1 mol, prepared according to N. L. J. M. Broekhof et al., *Tetrahedron Lett.*, 1979, 2433) in tetrahydrofuran (300 mL) under nitrogen at 0° C. The resulting clear red solution was stirred for 10 minutes at 0° C., and cyclopropanecarboxaldehyde (10A, 7.5 mL, 0.1 mol) added dropwise at 0° C. After 2 hours at 0° C., the resulting clear yellow solution was treated with saturated ammonium chloride. The organic layer was separated and the water layer extracted with methylene chloride. The combined organic layers were washed with water and dried (MgSO$_4$). Evaporation of solvent provided the alcohol adduct which was dried and added to a suspension of sodium hydride (2.75 g, 0.11 mol) in tetrahydrofuran (300 mL), and then stirred for 8 hours at 23° C. Pentane (1.5L) and water (300 mL) were added, and the reaction mixture was stirred overnight. The organic layer was separated, dried (MgSO$_4$) and concentrated to afford the crude product. Distillation of the crude product under high vacuum afforded the title compound as a colorless oil (1A, 7.5 g, 82%).

EXAMPLE 2

(Compound 2A, Scheme 3)

Preparation of Intermediate 2-cyclopropyl-1-(morpholin-4-yl)pent-1-en-3-one

To a sample of 1-(2-cyclopropylethenyl)morpholine (1A, 1.53 g, 10 mmol, from Example 1) and triethylamine (1.01 g, 10 mmol) in methylene chloride (80 mL) stirred at 0° C. under nitrogen, a solution of propionyl chloride (0.92 g, 10 mmol) in methylene chloride (40 mL) was added dropwise. The reaction mixture was then heated at reflux for 20 hours. The reaction mixture was cooled, washed with water, dried and concentrated to afford the title compound (2A, 133 mg, 64%). $^1$H NMR (300 MHz, CDCl$_3$): δ0.55 (m, 2H), 1.02 (m, 2H), 1.16 (t, 3H), 1.38 (m, 1H), 2.37 (q, 2H), 3.45 (t, 4H), 3.75 (t, 4H), 7.10 (s, 1H); MS (DCI/NH$_3$) m/e (M+H)$^+$210, (M+NH$_4$)$^+$217.

EXAMPLE 3

(Compound 3A, Scheme 3)

Preparation of Intermediate 1,2-dihydro-5-cyclopropyl-6-ethyl-2-oxo-3-cyanopyridine A sample of 2-Cyclopropyl-1-(morpholin-4-yl)pent-1-en-3-one (2A, 2.09 g, 10 mmol), cyanoacetamide (0.92 g, 11 mmol) and piperidine acetate (4 mL) were dissolved in ethanol (30 mL) under nitrogen. The reaction mixture was heated at reflux for 24 hours. The reaction mixture was cooled and concentrated, then diluted with methylene chloride. The solution was washed with brine and dried (MgSO$_4$), filtered and concentrated. The crude solid was chromatographed (silica, 5% methanol/methylene chloride) to afford pure title compound (3A, 1.54 g, 82%) as a crystalline solid. $^1$H NMR (300 MHz, CDCl$_3$): δ0.62 (m, 2H), 0.98 (m, 2H), 1.38 (t, 3H), 1.71 (m, 1H), 2.91 (q, 2H), 7.63 (s, 1H); MS (DCI/NH$_3$) m/e 189 (M+H)$^+$, 206 (M+NH$_4$)$^+$. Anal. Calcd for C$_{11}$H$_{12}$N$_2$O: C, 70.19; H, 6.42; N, 14.88. Found C, 70.31; H, 6.49; N, 14.62.

EXAMPLE 4

(Compound 4A, Scheme 3)

Preparation of Ethyl 1,2-dihydro-5-cyclopropyl-6-ethyl-2-oxo-3-pyridinecarboxylate Method 4A 1,2-Dihydro-5-cyclopropyl-6-ethyl-2-oxo-3-pyridinecarbonitrile (3A, 1.88 g, 10 mmol, from Example 3) was dissolved in absolute ethanol (3 mL) and the resulted solution was added to saturated ethanolic HCl (15 mL) at 0° C. under nitrogen. The reaction mixture was stirred at 0° C. for 3.5 hours, water (1.5 mL) was added and the reaction mixture was heated at 80° C. for 3 hours. After cooling, the reaction mixture was poured into cold water (70 mL), solid NaHCO$_3$ was added to adjust the solution to pH 8, and the mixture was extracted with methylene chloride (25 mL×3). The extract was washed with brine (20 mL) and dried (MgSO$_4$), filtered and concentrated. The residue was purified by chromatography (silica, 5% methanol/methylene chloride) to afford the title compound (4A, 1.9 g, 81%) as a crystalline solid. $^1$H NMR (300 MHz, CDCl$_3$): δ0.60 (m, 2H), 0.95 (m, 2H), 1.32 (t, 3H), 1.38 (t, 3H), 1.75 (m, 1H), 2.88 (q, 2H), 4.38 (q, 2H), 7.94 (s, 1H); MS (DCI/NH$_3$) m/e 236 (M+H)$^+$, 253 (M+NH$_4$)$^+$. Anal. Calcd for C$_{13}$H$_{17}$NO$_3$: C, 66.36; H, 7.28; N, 5.95. Found C, 66.59; H, 7.36; N, 6.17.

Method 4B

The 1,2-Dihydro-5-cyclopropyl-6-ethyl-2-oxo-3-pyridinecarbonitrile (3A, 2.09 g, 10 mmol, from Example 3) and carboxyethylacetamide (0.92 g, 11 mmol) were dissolved in piperidine acetate solution (4 mL) and ethanol (20 mL) under nitrogen. The reaction mixture was heated at reflux for 24 hours. After the reaction was complete, the reaction mixture was cooled to 20° C. and concentrated in vacuo. Methylene chloride was added, and the organic solution was washed with brine, dried (MgSO$_4$), filtered and concentrated. The crude solid was chromatographed (silica, 5% methanol/methylene chloride) to provide the title compound (4A, 1.24 g, 55%).

EXAMPLE 5

(Compound 5A, Scheme 3)

Preparation of Ethyl 5-cyclopropyl-6-ethyl-2-O-(tert-butyldimethylsilyl)-3-pyridinecarboxylate A solution of ethyl 1,2-dihydro-5-cyclopropyl-6-ethyl-2-oxo-3-pyridinecarboxylate (4A, 1.17 g, 5 mmol), TBSCl (0.82 g, 5.5 mmol), imidazole (0.68 g, 10 mmol), and DMAP (61 mg, 0.5 mmol) in DMF (15 mL) was stirred at room temperature for 24 hours. The mixture was then diluted with ethyl acetate, washed with water and brine, and dried (MgSO$_4$). The solution was concentrated and chromatographed (silica, methylene chloride) give the desired product (5A, 1.68 g, 96%). $^1$H NMR (300 MHz, CDCl$_3$): δ0.45 (s, 6H), 0.58 (m, 2H), 0.90 (m, 2H), 1.00 (s, 9H), 1.28 (t, 3H), 1.37 (t, 3H), 1.80 (m, 1H), 2.88 (q, 2H), 4.34 (q, 2H), 7.75 (s, 1H); MS (DCI/NH$_3$) m/e 350 (M+H)$^+$. Anal. Calcd for C$_{19}$H$_{31}$NO$_3$Si: C, 65.28; H, 8.93; N, 4.00. Found C, 65.58; H, 8.86; N, 4.17.

EXAMPLE 6

(Compound 6A, Scheme 3)

Preparation of Ethyl 5-cyclopropyl-6-[2-(4-penten-4-fluoro-5-ethoxy-3-one)]-3-pyridinecarboxylate Potassium hexamethyldisilazide (6 mL of 0.5M toluene solution, 3 mmol) was added dropwise to a solution of ethyl 5-cyclopropyl-6-ethyl-2-O-(tert-butyldimethylsilyl)-3-pyridinecarboxylate (5A, 0.7 g, 2 mmol) in tetrahydrofuran (20 mL) at −78° C. under nitrogen. After stirring for 1 hour at −78° C., the reaction mixture was warmed to −50° C. and stirred for 40 minutes. This solution was then added dropwise to 3-ethoxy-2-fluoroacryloyl chloride (14, R$^9$=ethyl, 0.3 g, 2 mmol) in tetrahydrofuran (20 mL) at −78° C. After stirring for 2 hours, the mixture was allowed to warm slowly to 0° C. and stirred for another 6 hours. Saturated ammonium chloride (2 g) was added and the solution was extracted with ether (20 mL×3) The organic extracts were combined, dried (Na$_2$SO$_4$), filtered and evaporated to give the title compound as an off, which was taken directly to the next step (Example 7) without further purification.

3-Ethoxy-2-fluoroacryloyl chloride (14, R$^9$=ethyl) was prepared as follows:

NaH (60% suspension in mineral oil, 15.6 g, 0.39 mole) was washed with and suspended in ether (300 mL). To this suspension, ethyl formate (29.1 mL, 0.36 mole, 1.2 eq) was added and the mixture was cooled in an ice bath. Ethyl fluoroacetate (29.0 mL, 0.3 mole) was added slowly over 1 hour. After 2 hours the ice bath was removed and the reaction was stirred for another hour. After evaporation of the solvent, the residue was redissolved in 350 mL of dry DMF and cooled in an ice bath, and ethyl iodide (48 mL, 0.6 mole) was added dropwise. The solution was allowed to warm to room temperature and stirred overnight, then quenched with saturated aqueous solution of NH$_4$Cl (100 mL). The mixture was diluted with ether and extracted with water. The separated ether layer was washed with sodium thiosulfate, brine and dried over MgSO$_4$. After concentration under vacuum, the residue was distilled to give ethyl 3-ethoxy-2-fluoroacrylate (12, R$^9$=ethyl, 73°–85° C./14 mmHg) as a colorless oil. $^1$H NMR (300 MHz, CDCl$_3$): δ1.35 (t, 3H), 1.39 (t, 3H), 4.10 (q, 2H), 4.30 (q, 2H), 6.95 (d, 1H).

The fleshly prepared ethyl 3-ethoxy-2-fluoroacrylate (12, R$^9$=ethyl, 16.49 g, 0.10 mole) was refluxed in 100 mL of 2N NaOH for 1 hour. After cooling to room temperature, the aqueous solution was washed with hexane (100 mL). The water layer was adjusted to pH 3–4 by addition of 10% HCl and extracted with a mixture of ether and ethyl acetate. The organic layer was washed with brine, dried over MgSO$_4$ and filtered. Evaporation of solvents yielded crude 3-ethoxy-2-fluoroacrylic acid (13, R$^7$=ethyl, 7.81 g, 0.054 mole) which was dissolved in 53 mL 1N NaOH, then water was evaporated and the residue was dried under vacuum at 85° C. overnight to give the sodium salt (13, R$^9$=ethyl). This salt was suspended in 100 mL of ether and treated with SOCl$_2$ (4.68 mL, 0.064 mole, 1.2 eq). After reflux for 6 hours, the mixture was concentrated and distilled to give 3-ethoxy-2-fluoroacryloyl chloride (14, R$^9$=ethyl, bp 102°–107° C./14 mmHg, 6.55 g).

EXAMPLE 7

(Compound 7A, Scheme 3)

Preparation of Ethyl 8-hydroxy-1-cyclopropyl-7-fluoro-9-methyl-4-oxo-4H-quinolizine-3-carboxylate Ethyl 5-cyclopropyl-6-[2-(4-penten-4-fluoro-5-ethoxy-3-one)]-3-pyridine-carboxylate (crude 6A, from Example 6) was dissolved in anhydrous toluene (10 mL), and a catalytic amount of toluenesulfonic acid monohydrate was added to the solution. The reaction mixture was refluxed under nitrogen for 2 hours. After cooling to room temperature, the desired product precipitated out as an off-white solid. Filtration afforded the title compound 7A (25 % yield from compound 5A). $^1$H NMR (300 MHz, DMSO-d$_6$): δ0.50 (m, 2H), 0.82 (m, 2H), 1.22 (t, 3H), 2.15 (m, 1H), 2.57 (s, 3H), 4.10 (q, 2H), 7.11 (d, 1H), 7.47 (d, 1H), 8.95 (d, 1H).MS (DCI/NH$_3$) m/e 306 (M+H)$^+$.

EXAMPLE 8

(Compound IIA, Scheme 3)

Preparation of ethyl 8-chloro-1-cyclopropyl-7-fluoro-9-methyl-4-oxo-4H-quinolizine-3-carboxylate Under nitrogen, ethyl 8-hydroxy-1-cyclopropyl-7-fluoro-9-methyl-4-oxo-4H-quinolizine-3-carboxylate (7A, 1.52 g, 5 mmol) was dissolved in methylene chloride (10 mL), and treated with DMF (0.73 g, 10 mmol) and POCl$_3$ (1.53 g, 10 mmol). After stirring overnight, the mixture was poured into 10 mL of ice water. The organic layer was separated, and the aqueous layer was extracted with methylene chloride (10 mL×2). The organic layers were combined, washed with saturated NaHCO$_3$ and brine, dried (MgSO$_4$), filtered and concentrated to give the crude product which was chromatographed (silica gel, 50% ethyl acetate/hexane) to give the title compound (IIA, 1.3 g, 80%). $^1$H NMR (300 MHz, CDCl$_3$): δ0.75 (m, 2H), 1.08 (m, 2H), 1.42 (t, 3H), 2.30 (m, 1H), 3.19 (s, 3H), 4.42 (q, 4H), 8.39 (s, 1H), 9.43 (d, 1H): MS (DCI/NH$_3$) m/e 324 (M+H)$^+$. Anal. Calcd for C$_{16}$H$_{15}$ClFNO$_3$: C, 59.35; H, 4.67; N, 4.32. Found C, 59.68; H, 4.76; N, 4.22.

What is claimed is:

1. A process for the preparation of a compound having the formula:

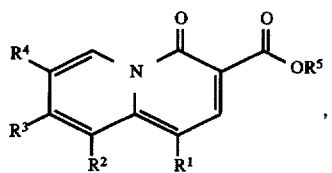

wherein $R^1$ is selected from the group consisting of $C_1$–$C_6$-alkyl, $C_2$–$C_6$-alkenyl, $C_2$–$C_6$-alkynyl, $C_3$–$C_6$-cycloalkyl, phenyl, fluorophenyl, difluorophenyl, nitrophenyl, dinitrophenyl, and fluoropyridyl, $R^2$ is $C_1$–$C_3$-alkyl or cyclopropyl, $R^3$ is chlorine, bromine, iodine, methylsulfonate, trifluoromethylsulfonate or toluenesulfonate, $R^4$ is fluorine, chlorine, bromine, or iodine, and $R^5$ is $C_1$–$C_6$-alkyl; the method comprising:

(a) treating a compound having the formula:

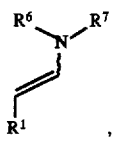

wherein $R^1$ is as defined above, $R^6$ and $R^7$ are $C_1$–$C_6$-alkyl, or $R^6$ and $R^7$ are taken together with the nitrogen atom to which they are connected to form a morpholinyl, pyrrolidinyl or piperidinyl ring, with an acid chloride $R^2$—$CH_2$—CO—Cl, wherein $R^2$ is as described above, and isolating a first intermediate compound having the structure:

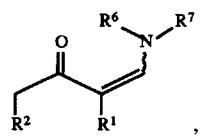

wherein $R^1$, $R^2$, $R^6$ and $R^7$ are as described above;

(b) treating the first intermediate compound sequentially with a base, then with 2-cyanoacetamide, and isolating a second intermediate compound having the structure:

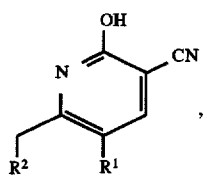

wherein $R^1$ and $R^2$ are as described above;

(c) hydrolyzing the cyano group of the second intermediate compound with an acid in an alcohol solvent $R^5$—OH, wherein $R^5$ is as described above, and isolating a third intermediate compound having the structure:

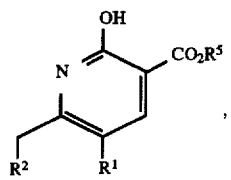

wherein $R^1$ and $R^2$ are as described above and $R^5$ is $C_1$–$C_6$-alkyl;

(d) treating the third intermediate compound with $R^8X$, wherein $R^8$ is $C_1$–$C_6$-alkyl, benzyl, substituted benzyl, or trialkylsilyl, and X is chlorine, bromine, iodine, methylsulfonate, trifluoromethylsulfonate or toluenesulfonate, and isolating a fourth intermediate compound having the structure:

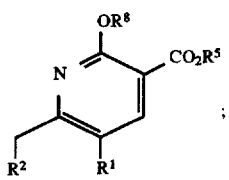

(e) treating the fourth intermediate compound sequentially with an alkali metal base, then with a 3-alkoxyacryloyl compound having the formula:

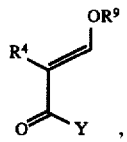

wherein $R^4$ is as described above, $R^9$ is $C_1$–$C_6$-alkyl and Y is chloride, bromide, cyano, alkoxy or imidazolyl and isolating a fifth intermediate compound having the structure:

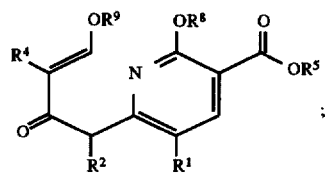

(f) cyclizing the fifth intermediate compound with a catalytic amount of acid, and isolating the sixth intermediate compound having the structure:

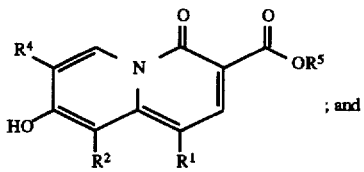

; and (g) treating the sixth intermediate compound with a halogenating or sulfonating agents, and isolating the desired compound.

2. A process according to claim 1 wherein $R^1$ is cyclopropyl, $R^2$ is methyl, $R^3$ is chloro, $R^4$ is fluoro, and $R^5$ is ethyl.

3. A process according to claim 1 wherein $R^6$ and $R^7$ are taken together with the atom to which they are connected to form a morpholinyl ring.

4. A process according to claim 1 wherein in step (a) the reaction is performed in the presence of a base at a temperature of from about −20° C. to about 80° C. for from about 4 to about 48 hours; in step (b), the reaction is performed at a temperature of about 23° C. to reflux for from about 4 to about 24 hours; in step (c) the reaction is performed at the reflux temperature of the solvent for about 4 to about 24 hours; in step (d) the reaction is performed at from about 0° C. to reflux temperature for from about 4 to about 48 hours; in step (e) the reaction is performed at about −78° C. to about 0° C. for about 2 to 6 hours; in step (f) the reaction is performed at reflux temperature for from about 4 to about 24 hours; and in step (g) the reaction is performed at room temperature for about 4 to about 24 hours.

5. A process according to claim 4 wherein $R^1$ is cyclopropyl, $R^2$ is methyl, $R^3$ is chloro, $R^4$ is fluoro, and $R^5$ is ethyl.

6. A process according to claim 4 wherein $R^6$ and $R^7$ are taken together with the atom to which they are connected to form a morpholinyl ring.

7. A process according to claim 1, wherein steps (b) and (c) are replaced by a single step wherein the first intermediate compound having the structure:

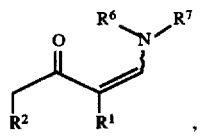

wherein $R^1$, $R^2$, $R^6$ and $R^7$ are as described above, is reacted with an ester of malonamic acid ($R^5$—O—CO—$CH_2$—CO—$NH_2$, wherein $R^5$ is as described above) in the presence of a base.

8. A process according to claim 7 wherein $R^1$ is cyclopropyl, $R^2$ is methyl, $R^3$ is chloro, $R^4$ is fluoro, and $R^5$ is ethyl.

9. A process according to claim 7 wherein $R^6$ and $R^7$ are taken together with the atom to which they are connected to form a morpholinyl ring.

10. A process according to claim 9 wherein in step (a) the reaction is performed in the presence of a base at a temperature of from about −20° C. to about 80° C. for from about 4 to about 48 hours and the first intermediate compound having the structure:

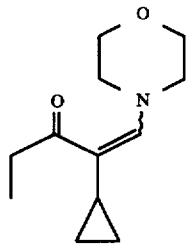

is reacted with the ethyl ester of malonamic acid in the presence of a base selected from potassium carbonate, piperidine acetate, piperidine, triethylamine, and sodium ethoxide at a temperature of about 23° C. to reflux for about 4 to about 24 hours to prepare the intermediate compound having the formula:

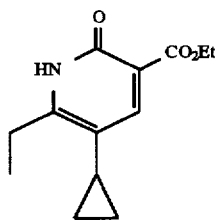

in step (d) the reaction is performed at reflux temperature for from about 4 to about 48 hours; in step (e) the reaction is performed at about −78° C. to about −50° C. for about 20 to about 120 minutes; in step (f) the reaction is performed at reflux temperature for from about 4 to about 24 hours; and in step (g) the reaction is performed at a temperature from about 0° C. to reflux for about 4 to about 24 hours.

* * * * *